(12) United States Patent
Afanasiev et al.

(10) Patent No.: US 7,585,995 B2
(45) Date of Patent: Sep. 8, 2009

(54) CONTINUOUS WASTELESS ECOLOGICALLY SAFE TECHNOLOGY OF PROPYLENECARBONATE PRODUCTION IN PRESENCE OF PHTHALOCYANINE CATALYSTS

(75) Inventors: Vladimir Vasilievich Afanasiev, Moscow (RU); Nikolai Serafimovich Zefirov, Moscow (RU); Dmitry Yurievich Zalepugin, Moscow (RU); Victor Stanislavovich Polyakov, Moscow (RU); Nataliya Alexandrovna Tilkunova, Moscow (RU); Larisa Godvigovna Tomilova, Moscow (RU)

(73) Assignee: U.S. Department of Energy, Washington, DC (US)

( * ) Notice: Subject to any disclaimer, the term of this patent is extended or adjusted under 35 U.S.C. 154(b) by 525 days.

(21) Appl. No.: 11/533,779

(22) Filed: Sep. 21, 2006

(65) Prior Publication Data

US 2007/0078268 A1    Apr. 5, 2007

Related U.S. Application Data

(60) Provisional application No. 60/720,461, filed on Sep. 27, 2005.

(51) Int. Cl.
*C07C 69/96* (2006.01)
*C07D 317/08* (2006.01)
(52) U.S. Cl. ..................... 558/260; 549/230
(58) Field of Classification Search ............... None
See application file for complete search history.

(56) References Cited

U.S. PATENT DOCUMENTS 5,283,356 A * 2/1994 Marquis et al. ............ 558/260

* cited by examiner

*Primary Examiner*—Kamal A Saeed
(74) *Attorney, Agent, or Firm*—Annette R. Reimers; Julia C. Moody; Paul A. Gottlieb

(57) ABSTRACT

A continuous method of producing propylenecarbonate includes carboxylation of propylene oxide with carbon dioxide in presence of phthalocyanine catalyst on an inert carrier, using as the phthalocyanine catalyst at least one catalyst selected from the group consisting of not-substituted, methyl, ethyl, butyl, and tret butyl-substituted phthalocyanines of metals, including those containing counterions, and using as the carrier a hydrophobic carrier.

8 Claims, No Drawings

CONTINUOUS WASTELESS ECOLOGICALLY SAFE TECHNOLOGY OF PROPYLENECARBONATE PRODUCTION IN PRESENCE OF PHTHALOCYANINE CATALYSTS

CROSS REFERENCE TO RELATED APPLICATIONS

This application claims priority from Provisional U.S. application Ser. No. 60/720,461 filed Sep. 27, 2005 and Russian application S.N. 2006118131 filed May. 26, 2006.

BACKGROUND OF THE INVENTION

The present invention relates to a continuous method of producing propylenecarbonate in a reaction of propylene oxide with carbon dioxide in presence of phthalocyanine catalysts in accordance with the scheme:

The development of ecologically safe and highly efficient method for producing propylenecarbonate is an important task, since it is a raw material for obtaining of a new generation polymer, namely polypropylenecarbonate.

Polypropylenecarbonate is a polymer which is used for producing laser disks, control panels in cabins of modern airplanes. It has unique strength properties, long service life and fire resistance. The technology of its manufacture nowadays is very expensive and not sufficiently developed.

A raw material for producing polypropylenecarbonate is propylene oxide. Propylene oxide is characterized by linking reactions, which are enhanced by a relative easiness of opening of the cycle. The most used reaction is hydration with formation of propyleneglycol and also di-, tri- and polyglycols as byproducts. The hydration of propylene oxide with the use of $CO_2$ (120-160° C., 0.5-4 MPa) is performed selectively with formation of monopropyleneglycol; an intermediate product is propylene carbonate.

Reactions of alkylene oxides and carbon dioxide in presence of catalysts are known and disclosed in U.S. Pat. Nos. 2,773,070; 2,873,282; 3,535,341; 4,786,741; European patent no 0297647, and Japanese patent no. 63-181765.

As a rule, it was proposed to use as catalysts for reactions in substantially high concentrations-halogen-containing compounds, whose use led to production of alkylene carbonates, that contain a great quantity of halogen-containing admixtures. In addition, the majority of proposed catalysts loose their activity in these reactions or contribute to interaction of epoxydes with each other, and not with carbon dioxide. It is therefore necessary to use catalysts, which are not destroyed in the process of linking of carbon dioxide, do not introduce impurities into reaction products, and allow to efficiently link carbon dioxide.

A method of producing alkaline carbonates with the use of phthalocyanines of metals as catalysts is disclosed in U.S. Pat. No. 5,283,356.

This method has the disadvantage of low solubility of the used catalysts, which leads most probably to hetergenous course of the process with a significantly lower efficiency. Moreover, conducting the reaction in hetergenous conditions does not allow to achieve quantitative linking of carbon dioxide, which correspondingly significantly reduces the efficiency of the method.

This disadvantage was eliminated with the use of tert-butyl-substituted phthalocyanine complexes as catalysts, whose solubility is several orders higher than solubility of its non-substituted analogs, as disclosed in patent no. 2,100,355 of Russian Federation.

This method however, as all above mentioned methods, require to conduct experiments in static and significantly hard conditions, in particular in an autoclave with temperature 180° C. during two hours. Moreover, the used catalyst did not have a significantly expanded surface, that reduced the reaction and led to fast poisoning of the catalyst.

A continuous method of producing of polypropylenecarbonate in presence of the phthalocyanine catalysts by carboxylation of propylene oxide was proposed with the use of an inert carrier, in particular granulated adsorbent celite 535, which has the following characteristics: chemical composition-silicium acid with low quantity of oxides Al, Fe, Mg, Ca, specific surface 1-3 $m^2$/g, particulate density approximately 0.24 g/$cm^3$, average pore diameter 1-3 µm, granule diameters 60-80 mesh. As a catalyst tert-butyl substituted phthalocyanine aluminum chloride PctAlCl or its non-substituted analog PcAlCl were used. The reaction was conducted in a temperature range of 100-150° C., with a pressure in a reactor 20-40 atm. The supply of C02 (gas) was 12 g/hour, of propylene oxide 0.1 g/hour. Mol ratio C02/propylene oxide was approximately 144/1. Time of conducting the process until complete loss of catalyst activity was 16-24 hours. Average yield during the time of conducting the reaction was 2-7% of propylenecarbonate relative to a mass of propylene oxide, depending on used catalyst. It is disclosed in patent no. 2,228, 933 of Russian Federation.

This method however requires a frequent change of the spent catalyst, and the yield of the final product and process of linking of carbon dioxide did not satisfy the conditions of modern manufacture.

SUMMARY OF THE INVENTION

It is an object of the present invention to provide a method of continuous wasteless ecologically safe technology of propylenecarbonate production in presence of phthalocyanine catalysts, which is a further improvement of the existing methods.

In keeping with these objects and with others which will become apparent hereinafter, one feature of the present invention resides, briefly state, in a method of continuous wasteless ecologically safe technology of propylenecarbonate production in presence of phthalocyanine catalysts on inert carrier, wherein as phthalocyanine catalysts at least a catalyst selected from the group consisting of non-substituted, methyl-, ethyl, butyl-, and tert-butyl substituted phthalocyanines of metals are used, and as a carrier a hydrophobic carrier is used.

When the method is performed in accordance with the present invention, the yield of the product is increased 2-3 times, and the service life of the catalyst is increased more than by 70%, while the percent of linking of carbon dioxide increases 2-3 times.

As a result of multiple experiments it has been determined that the non-substituted, methyl, ethyl, butyl, and tret butyl substituted phthalocyanines of these elements, applied on the hydrophobic carrier, are the most efficient catalysts for the continuous process of obtaining propylenecarbonate by carboxylation of the propylene oxide with carbon dioxide.

The use as a carrier of the hydrophobic carrier excludes the possibility of presence in the reaction zone of even trace quantities of water, which, as was determined, is a negative factor enhancing the formation of olygomeric and polymeric products on the surface of catalyst, which leads to its "poisoning".

From the known hydrophobic carriers, the known most acceptable for the inventive method is silanized glass. Silanized glass can be used in form of balls, rings or pipes.

One of the variants of the catalytic system which allows to increase yield of the final product is the use as a catalyst phthalocyanine aluminum chloride PcAlCl.

The high yield of the product is also obtained with the use of phthalocyanines of chromium and ruthenium as the catalyst.

The optimal parameters of the process are as follows:

Pressure 40-90 atm, temperature 130-200° C., use of C02 within range of 5-10 ml/min, and use of propylene oxide within range of 30-40 mg/hour.

The most optimal is the ratio of 0.12% of the mass of catalyst to the total mass of catalytic system.

The continuous process of obtaining of propylenecarbonate was carried out in a corresponding apparatus. Propylene oxide was supplied into a mixer by means of a pump, and from a container gaseous C02 was supplied as well into the mixer, while the flow of gas was adjusted by a valve. The obtained mixture was supplied to a reactor filled with a catalyst, where an interaction of the reactants took place. The reaction mixture was processed in a separator, in which propylenecarbonate was separated, and the process was regulated by a valve. After passing through the separator, non-reacted propylene oxide was condensed in a refrigerator and returned again into a container (C02 as a gas was vented into atmosphere). For evaporation of propylene oxide, the separator was heated to 90° C. After the catalysts were completely spent in the reactor, the flow of mixture C02-propylene oxide, by means of a flow switch, was supplied to a parallel reactor, filled with a fresh catalyst. The spent catalyst was discharged from the reactor and regenerated. The yield of propylenecarbonate and its purity were determined by gas-chromatograph. The conditions of analysis: gas-chromatograph Vartan 3700 with a plasma-ionization detector, a capillary column with length 30 m, DB-5 (SE-30), d=0.32 mm, a carrier gas-nitrogen, T evap–250° C., Tdet–220° C., the program of column thermostat 40° C. (3 minutes)–250° C., 12°/min. The conducted analysis showed that in the process of carboxylation in the separator polypropylenecarbonate was separated with purity about 98% and containing a small quantity of propyleneglycol, dimers and trimers of propylenecarbonate.

The following catalysts were tested:

Non-substituted phthalocyanines of ruthenium (PcRu), aluminum with antiion of chlorine (PcAlCl) and zinc (PcZn), methyl-substituted phthalocyanines of disporosium ($^{Me}$PcDy), manganese ($^{Me}$PcMn), ethyl-substituted phthalocyanines of therbium ($^{Et}$PcTb) and lutecium ($^{Et}$PcLu), buthyl-substituted phthalocyanines of zinc ($^{Bu}$PcZn), and manganese ($^{Bu}$PcMn), and tret-butyl-substituted phthalocyanines of chromium $^{tBu}$PcCr, ruthenium $^{tBu}$PcRu and aluminum $^{tBu}$PcAlCl.

The results of the tests are presented in the table.

TABLE 1

| Catalyst | P(atm) | T(° C.) | Time (min) | Charge of Catalyst (g) | Conversion ((mpk/mop) × 100%)* |
|---|---|---|---|---|---|
| $^{tBu}$PcAlCl | 60 | 140 | 15 | 0.0125 | 17.3 |
| $^{Me}$PcDy | 60 | 140 | 15 | 0.0125 | 4.5 |
| $^{Me}$PcMn | 60 | 140 | 15 | 0.0114 | 6.2 |
| PcAlCl | 60 | 140 | 15 | 0.0194 | 12.2 |
| PcZn | 60 | 140 | 15 | 0.0126 | 4.6 |
| $^{tBu}$PcRu | 60 | 140 | 15 | 0.0124 | 15.4 |
| $^{Et}$PcTb | 60 | 140 | 15 | 0.0118 | 4.5 |
| $^{Et}$PcLu | 60 | 140 | 15 | 0.0069 | 3.3 |
| $^{Bu}$PcZn | 60 | 140 | 15 | 0.0069 | 2.2 |
| $^{Bu}$PcMm | 60 | 140 | 15 | 0.0069 | 12.5 |
| $^{tBu}$PcCr | 60 | 140 | 15 | 0.0126 | 14.0 |
| PcZn | 60 | 140 | 15 | 0.0156 | 6.7 |
| PcMn | 60 | 140 | 15 | 0.0147 | 4.7 |

*relationship of mass of obtained propylenecarbonate to mass of propylene oxide in percentages.

From the data presented in Table it is possible to make an conclusion that all above mentioned phthalocyanines exhibit substantially high activity in reaction of carboxylation of propylene oxide. Especially high activity is exhibited in reaction of carboxylation of propylene oxide with catalysts $^{tBu}$PcAlCl, $^{tBu}$PcRu and $^{tBu}$PcCr.

The examples presented hereinabove, confirm, but do not limit the proposed method of obtaining propylenecarbonate by carboxylation of propylene by carbon dioxide in presence of phthalocyanine catalysts.

EXAMPLE 1

Reaction of carboxylation was performed in an apparatus in accordance with the scheme presented herein above. As the catalytic system, "silanized glass balls diameter 2mm+ PcAlCl" were used. The parameters of the process: Pressure 60 atm, temperature 180° C., ratio of mass of catalyst PcAlCl to a total mass of the catalytic system 0.12% (17 mg of catalyst distributed over the surface 14.01 g attachment). Use of C02-600 ml/hour (26.8 mMol/hour). The use of propylene oxide 37 mg/hour (0.64 mMol/hour).

Carrying of the process in these conditions allows to stably obtain propylenecarbonate with purity 98.8 with average mass yield 12.2% relative to propylene oxide during the whole time of experiment (39 hours). It should be mentioned that this time was not limiting for operation of the catalytic system, but just a temporary range studied in the above described experiment.

EXAMPLE 2

The same as in Example 1, but as a catalytic system "silanized glass in form of rings (attachment Fenske+$^{tBu}$PcAlCl" was used and the process was performed with pressure 40 atm, temperature 130° C., use of $CO_2$ 5 ml/min and use of propylene oxide 30 mg/hour. The yield of propylenecarbonate with purity 98.8 was 17.3% relative to propylene oxide during all time of experiment (39 hours).

EXAMPLE 3

The same as in example 1, but as a catalytic system "silanized glass in form of balls (diameter 2 mm)+$^{tBu}$PcRu" was used, and the process was carried out with pressure 90 atm, temperature 200° C., use of C02-10 ml/min, and use of propylene oxide 30 mg/hour. The yield of propylenecarbonate with purity 98.8 was 15.4% relative to propylene oxide during all time of experiment (39 hours).

EXAMPLE 4

The same as in Example 1 but as a catalytic system, a "silanized glass in form of rings (attachment Fenske)+

$^{tBu}$PcCr" was used, and the process was carried out with pressure 60 atm, temperature 180° C., use of C02-10 ml/min and use of propylene 35 mg/hour. Yield of propylenecarbonate with purity 98.8% was 40.0% relative to propylene oxide during all A use of experiment (39 hours).

EXAMPLE 5

The same as in Example 1, but as the catalytic system "silanized glass tubes with diameter 2 mm+PcAlCl" was used, and the process was carried out with pressure 40 atm, temperature 130° C., use of C02-5 ml/min, and use of propylene oxide 35 mg/hour. Yield of propylenecarbonate with purity 98.8% was 12.2% relative to propylene oxide during all time of experiment (39 hours).

FIG. 2 show data that characterize the influence of the ratio of mass of catalyst-phthalocyanine aluminum chloride to the total mass of the catalytic system.

TABLE 2

| Ratio of Mass of Catalyst Phthalocyanine Aluminum Chloride to Total Mass of Catalytic System % | Yield of Propylene carbonate % |
|---|---|
| 0.08 | 10 |
| 0.10 | 10 |
| 0.12 | 12.2 |
| 0.14 | 9.5 |
| 0.16 | 9.5 |

As can be seen from the table, the ratio of the mass of catalyst phthalocyanine aluminum chloride to the total mass of the catalytic system equal to 0.12 is an optimal ratio; however, this factor is not significant during the carrying out of the process.

EXAMPLE 6

The same as in Example 1, but as the catalytic system a "silanized glass in form of rings (attachment Fenske)+$^{tBu}$PcAlCl was used and the process was carried with pressure 90 atm, temperature 200° C., use of $CO_2$ 5 ml/min, use of propylene oxide 40 mg/hour. Yield of propylenecarbonate with purity 98.8% was 15.4% relative to propylene oxide during all time of experiment (39 hours).

EXAMPLE 7

The same as in Example 1 but as the catalytic system "silanized glass balls with diameter 2 mm+$^{tBu}$PcRu" were used and the process was carried out with pressure 60 atm, temperature 160° C., use of $CO_2$ 5 ml/min and use of propylene oxide 40 mg/hour. Yield of a propylenecarbonate with purity 98.8% was 13.3% relative to propylene oxide during all time of the experiment (39 hours).

TABLE 3

Shows the data which characterize the influence of parameters of the process on the yield of the final product.

| Pressure Atm | Temperature ° C. | Use Co2 ml/min | Use of propylene oxide mg/hour | Yield of Propylene carbonate % |
|---|---|---|---|---|
| 30 | 150 | 7 | 35 | 12.5 |
| 40 | 150 | 7 | 35 | 13.3 |
| 60 | 150 | 7 | 35 | 13.3 |
| 90 | 150 | 7 | 35 | 13.4 |
| 100 | 150 | 7 | 35 | 12.0 |
| 60 | 120 | 7 | 35 | 11.9 |
| 60 | 130 | 7 | 35 | 13.2 |
| 60 | 150 | 7 | 35 | 13.3 |
| 60 | 200 | 7 | 35 | 13.3 |
| 60 | 210 | 7 | 35 | 12.0 |
| 60 | 150 | 3 | 35 | 11.8 |
| 60 | 150 | 5 | 35 | 13.3 |
| 60 | 150 | 7 | 35 | 13.3 |
| 60 | 150 | 7 | 35 | 13.3 |
| 60 | 150 | 10 | 25 | 13.3 |
| 60 | 150 | 12 | 25 | 12.3 |
| 60 | 150 | 7 | 25 | 12.1 |
| 60 | 150 | 7 | 30 | 13.3 |
| 60 | 150 | 7 | 35 | 13.3 |
| 60 | 150 | 7 | 40 | 13.3 |
| 60 | 150 | 7 | 42 | 12.6 |

As can be seen from the table, pressure 40-90 atm, temperature 130-200° C., use of CO2 within the range 5-10 ml/min and use of propylene oxide within the range 30-40 mg/hour are optimal, but these factors are not significant during carrying out of the process.

EXAMPLE 8

The same as in Example 1, but as the hydrophobic carrier a "silanized glass in form of rings (attachment Fenske) $^{tBu}$PcCr" was used and in the process was carried with pressure 60 atm, temperature 150° C., use of C02 10 ml/min and use of propylene oxide 40 g/hour. Yield of propylene carbonate with purity 98.8 was 12.3% relative to propylene oxide during all time of experiment (39 hours).

The above presented examples show that the best result was obtained with the use of the catalytic system $^{tBu}$PcAlCl, whose use allowed to carry out the process of carboxylation during 39 hours with the maximum yield.

Therefore, the present invention represents a technologically convenient method for producing propylenecarbonate in relatively soft conditions-pressure 40-60 atm, temperature 130-200° C., with yield 17% relative to propylene oxide.

The reaction product has the purity about 98% and can be used for obtaining polypropylenecarbonate without additional purification.

It will be understood that each of the elements described above, or two or more together, may also find a useful application in other types of methods differing from the types described above.

While the invention has been illustrated and described as embodied in a continuous wasteless ecologically safe technology of propylenecarbonate production in presence of phthalocyanine catalysts, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. A continuous method of producing propylenecarbonate, comprising the steps of carboxylation of propylene oxide with carbon dioxide in presence of phthalocyanine catalyst on an inert carrier; using as the phthalocyanine catalyst at least one catalyst selected from the group consisting of not-substituted, methyl, ethyl, butyl, and tret butyl-substituted phthalocyanines of metals, including those containing counterions; and using as the carrier a hydrophobic carrier.

2. A continued method as defined in claim 1; and further comprising using silanized glass as the hydrophobic carrier.

3. A continued method as defined in claim 2; and further comprising using the silanized glass in a form selected from the group consisting of balls, rings and pipes.

4. A continued method as defined in claim 1; and further comprising using as the catalyst a phthalocyanine catalyst of aluminum chloride.

5. A continued method as defined in claim 1; and further comprising using as the catalyst a phthalocyanine of chromium.

6. A continued method as defined in claim 1; and further comprising using as the catalyst a phthalocyanine of ruthenium.

7. A continued method as defined in claim 1; and further comprising carrying out a process at a pressure 40-90 atm, temperature 130-200° C., use of $CO_2$ within a range 5-10 ml/min and use of propylene oxide within a range 30-40 mg/hour.

8. A continued method as defined in claim 1; and further comprising selecting a ratio of a mass of the catalyst to a total mass of a catalytic system of substantially 0.12%.

* * * * *